United States Patent
Lim

(10) Patent No.: US 10,271,781 B2
(45) Date of Patent: Apr. 30, 2019

(54) PLASTIC BLOOD LANCET

(71) Applicant: Chee Yen Lim, Singapore (SG)

(72) Inventor: Chee Yen Lim, Singapore (SG)

( * ) Notice: Subject to any disclaimer, the term of this patent is extended or adjusted under 35 U.S.C. 154(b) by 319 days.

(21) Appl. No.: 14/437,283

(22) PCT Filed: Nov. 5, 2012

(86) PCT No.: PCT/SG2012/000419
§ 371 (c)(1),
(2) Date: Apr. 21, 2015

(87) PCT Pub. No.: WO2014/070103
PCT Pub. Date: May 8, 2014

(65) Prior Publication Data
US 2015/0265198 A1    Sep. 24, 2015

(51) Int. Cl.
*A61B 5/00* (2006.01)
*A61B 5/151* (2006.01)
*A61B 5/15* (2006.01)

(52) U.S. Cl.
CPC ...... *A61B 5/15101* (2013.01); *A61B 5/15105* (2013.01); *A61B 5/15142* (2013.01);
(Continued)

(58) Field of Classification Search
CPC .. A61B 5/151; A61B 5/15142; A61B 5/15176
See application file for complete search history.

(56) References Cited

U.S. PATENT DOCUMENTS 8,211,133 B2 * 7/2012 Marshall .......... A61B 5/150022
606/181

8,377,088 B2 * 2/2013 Nicholls .......... A61B 5/15146
606/181

(Continued)

FOREIGN PATENT DOCUMENTS

EP         0447726 A1     9/1991
WO    WO 03066140 A1     8/2003

OTHER PUBLICATIONS

MatWeb Material Property Data [online] [retrieved on Jun. 21, 2013]. Retrieved from the Internet, URL: <http://www.matweh.com/Search> Groups. Liquid Crystal Polynmers, Polyethylene.

*Primary Examiner* — Max Hindenburg
(74) *Attorney, Agent, or Firm* — Cahn & Samuels, LLP

(57) ABSTRACT

The present invention provides a surgically invasive pointed article for skin penetration and capillary whole blood extraction whose penetration ability can be disabled after use by deforming the tips. The present invention is made by injection molding a plastic needle 35 having an anchoring means 45 using a first material, followed by another injection molding process to over-mold a first body segment 20 and second body segment 30 using a second material to encase the plastic needle 35 thereby anchoring the plastic needle 35 to prevent further movement of the plastic needle 35. The encasing of the second material provide a barrier isolating the plastic needle 35 from the ambient to protect the tips 50 from damage and once sterilized, to conserve the sterile conditions till point of use. The barrier formed by a second over-molding process comprises a detachable cap 20 and a body 30. The present invention is normally used for blood sampling applications but can also be used for applications such as vaccination or skin allergy testing, and transdermal/intradermal drug delivery.

4 Claims, 4 Drawing Sheets

(52) U.S. Cl.
CPC .. *A61B 5/150282* (2013.01); *A61B 5/150297* (2013.01); *A61B 5/150564* (2013.01); *A61B 5/150618* (2013.01); *A61B 5/150717* (2013.01); *A61B 5/150022* (2013.01); *A61B 5/150312* (2013.01); *A61B 5/150412* (2013.01); *A61B 5/150503* (2013.01)

(56) References Cited

U.S. PATENT DOCUMENTS

| | | | |
|---|---|---|---|
| 8,603,126 B2 * | 12/2013 | Nicholls | A61B 5/150427 606/181 |
| 2002/0168290 A1 | 11/2002 | Yuzfiakov et al. | |

* cited by examiner

PLASTIC BLOOD LANCET

BACKGROUND OF THE INVENTION

Field of the Invention

This invention relates generally to blood lancet which is used to prick a skin site for obtaining small volume of capillary whole blood for subsequent blood testing.

Background of the Invention

Skin penetration is insertion of at least a pointed article into the skin with depths ranging from tens of microns to less than three millimeters. Depending on the purpose, there are several methods and devices currently available for skin penetration. For transdermal drug delivery purpose, small cluster of needles (microneedles) are inserted into the skin to puncture the outer layer of skin which is otherwise a barrier for drug delivery into the skin. The term 'drugs' is, a general referred to medicinal substance such as hormones, drugs, vaccines etc. Such microneedles are sometimes inserted into the skin by bare hand or a hand held device to extract bodily fluids such as plasma etc. for analysis. Most of these devices and methods are still in clinical trial phase and are not available on the market. These devices are normally made in sophisticated processes. In addition, they require extra packaging effort in keeping them sterile till point of use and extra care for disposal to prevent accidental injuries or re-use.

For blood sampling purpose, the pointed article (better known as blood lancets, normally with needle length of 3 mm) is used with a spring-operated applicator which inserts the blood lancet into the skin and retracts it at a very high speed. Since the speed is very high (often more than 1,000 mm/sec), the duration of the blood lancet staying in the skin is very brief (often a few milliseconds), so the discomfort or pain incurred is minimal. The applicator's distal end which contacts the skin has an opening for the lancet to penetrate the skin. The opening also serves an important role in fixing the skin such that certain rigidity and surface tension are reached for optimal skin penetration. Without the fixation of the skin, the skin penetration result will be inconsistent and much more painful.

The current blood lancets are made by over-moulding a stainless steel needle with inexpensive polymer such as polyethylene or polypropylene to form a handle. A cap, which can be moulded separately or integrally moulded, is put on the tip to conserve the sterile conditions till point of use. Due to the slenderness of the stainless steel needle, there is no anchoring or fastening of it to the plastic body, making it vulnerable to slip out of the body. Slippage of the stainless steel needle will make the effective length longer than designed and will cause extra pain or injuries. There is also no prevention for accidental injuries and re-use after the blood lancets are disposed of, except that users are advised to dispose the used lancets in a sharps collector. The stainless steel needles remain sharp which may pose a great potential threat to the personnel handling the disposal. There is also a possibility that the used needles are collected for re-use.

Moreover, the current stainless steel lancet with plastic body have many manufacturing steps and different machines, such as handling and making the stainless steel needle, before moulding a plastic body and cap to encase the stainless steel needle. This inevitably drives up the cost of the blood lancets. In addition, the device comprising stainless steel and polymer is difficult to recycle as the stainless steel (1200 degree Celsius) has much higher melting temperature to polymers (<350 degree Celsius). In addition, the stainless steel needle imposes an injury threat to the medical personnel who handle the disposal of the lancets. The cap is not an adequate measure in preventing accidental injuries or re-use because it may not be capped after use or may be removed accidentally or intentionally.

Closest Prior Art

U.S. Pat. No. 8,211,133 B2 to Owen Mumford Limited reported a blood lancet made by liquid crystal polymer LCP which is encased by a second polymer polyethylene. The prior art did not consider a few critical issues in manufacturing and product design.

For example, the prior art did not consider the softening of LCP during the second over-moulding process with polyethylene PE. PE has melting temperature of 105-110° C. It is common to have a higher melt temperature to ensure good flow of the polymer. The glass transition temperature of LCP which is around 97-131° C., which means during the second moulding process to mould PE over LCP, the high temperature of melt PE and high injection pressure will cause deformation of the LCP particularly at the needle tip.

The prior art also failed to provide an effective design for removing the cap and exposing the needle before use. The design is identical to a blood lancet with stainless steel which requires twisting of the cap to remove the cap and expose the needle. For the stainless steel lancet, the twisting will not damage the needle because it is made of stainless steel. However, for the LCP lancet, the twisting may bend or distort the needle tip because the needle is extremely vulnerable at this size and that the twisting is often combination of random lateral and torsional movements. A damaged tip will not penetrate the skin at all or will cause extra pain to the user.

It is obvious that the current design of stainless steel lancets and the prior arts do not adequately provide a good solution for blood lancet design and manufacturing. In the present invention, the two issues that the prior art failed to consider will be fully addressed. The present invention incorporates the disclosure of PCT/SG 2001/000391 in its entirety.

Solutions to Exiting Problems and Prior Arts

1. The current blood lancets incorporate a stainless steel needle which is not anchored to the body, which means the needle may slip out due to vibration or expansion of the plastic body during transportation or storage. Such slippage will make the needle length longer than designed thereby causing extra pain or injuries. The present invention provides a plastic needle design that can be anchored onto the body so that such slippage risk is eliminated.
2. The current blood lancets have either no or inadequate safety measure in preventing accidental injuries and re-use after the blood lancets are disposed of. The used needles remain sharp and can pose injury threat to the personnel handling the disposal or be re-collected and re-used. The present invention provides a plastic tip which can be disabled after use, posing no threat to the personnel handling the disposal and eliminating the possibility of re-use.
3. The stainless steel blood lancets not cost efficient in terms of manufacturing and packaging, since they are disposable items, they should be made in a simple manufacturing process so that the cost can be brought down significantly. The present invention does not incur costs relating to cutting and grinding of stainless steel needles and employs only two injection moulding steps.

4. The LCP material for moulding the needle has too low the glass transition temperature compared to the melting temperature of PE, the second polymer for moulding the body and the cap. The present invention specifies the right material having a glass transition temperature which is higher than the melting temperature of the second polymer forming the body and the cap. This will prevent the deformation of the needle tip during production.

5. The twisting of cap over a plastic needle will bend or distort the needle tip. The present invention has a design feature that ensure that the cap is removed by pulling, not twisting of the cap.

SUMMARY OF THE INVENTION

The present invention provides a surgically invasive pointed article for skin penetration and capillary whole blood extraction whose penetration ability can be disabled after use by deforming the tips. The present invention, identified as a plastic blood lancet, is made by injection moulding a plastic needle having an anchoring means using a first material, followed by another injection moulding process to over-mould a second material to encase the plastic needle thereby anchoring the plastic needle to prevent further movement of the plastic needle. The encasing of the second material provide a barrier isolating the plastic needle from the ambient to protect the tips from damage and once sterilized, to conserve the sterile conditions till point of use. The barrier formed by a second over-moulding process comprises a detachable cap and a body. The present invention is normally used for blood sampling applications but can also be used for applications such as vaccination or skin allergy testing, and transdermal/intradermal drug delivery.

DESCRIPTION OF THE INVENTION

Detailed Description of the Invention

Figure 1:
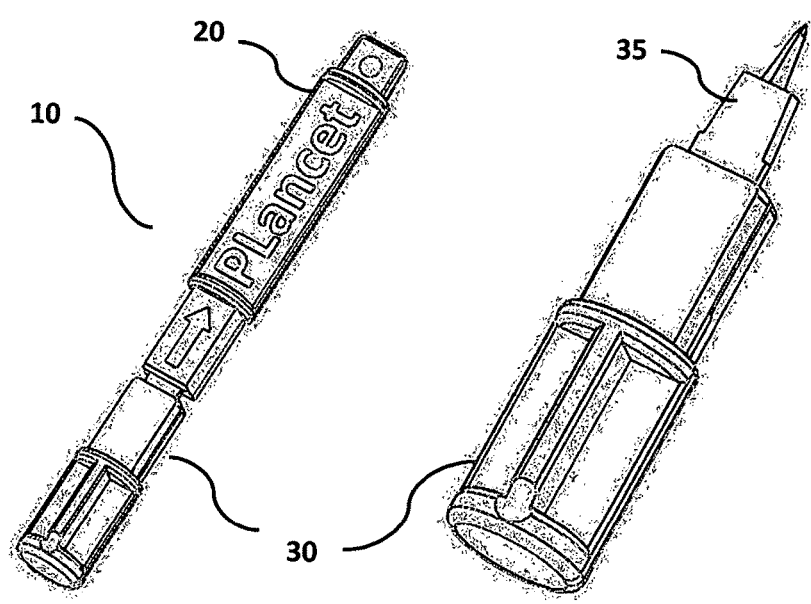
FIG. 1 illustrates a perspective view of a plastic blood lancet
Figure 2:
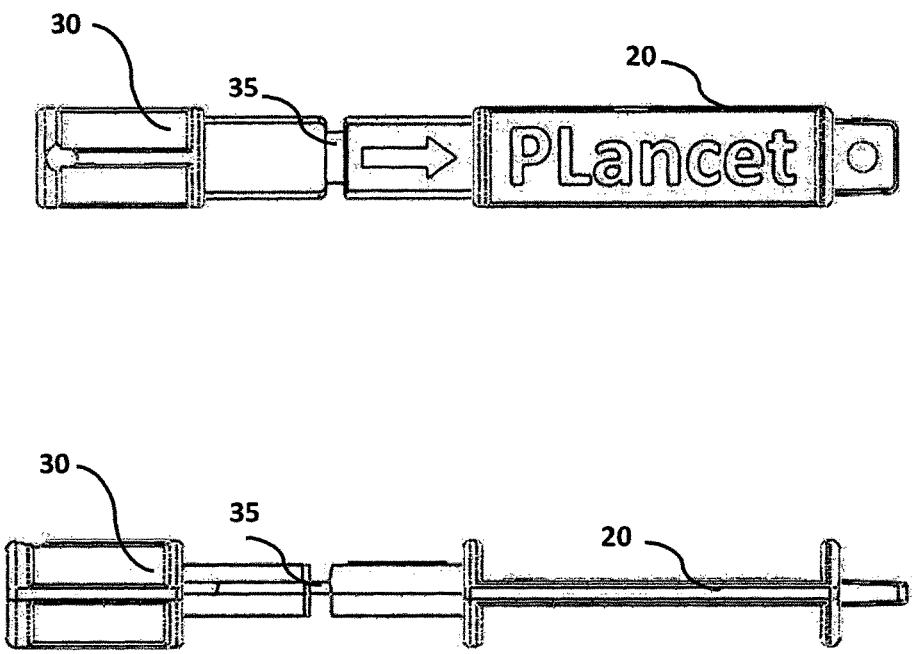
FIG. 2 illustrates a plan view and a side view of a plastic blood lancet
Figure 3:
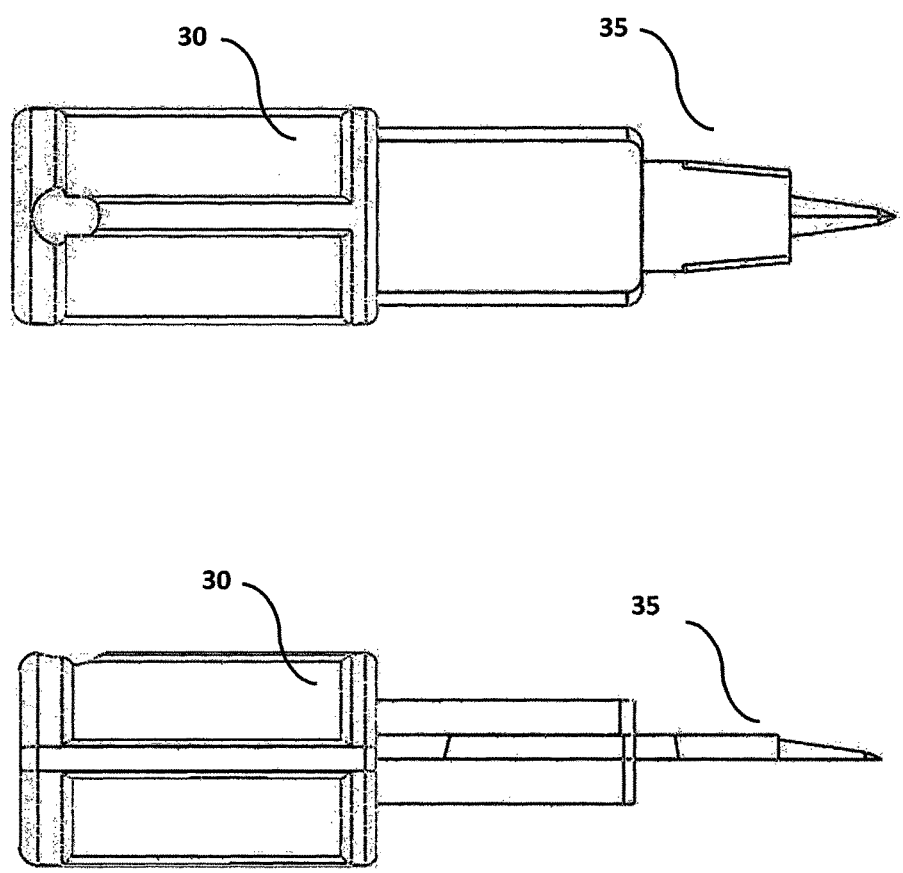
FIG. 3 illustrates a plan view and a side view of a plastic needle

The preferred embodiment of the present invention involves a surgically invasive skin penetration device 10 comprising at least three body segments, as shown in FIG. 1. The first body segment 20 comprises a cap to be removed to expose the plastic needle before use, the second body segment 30 comprises a body portion which is separated from the first body segment 20 and which has a shape and size suitable for handling and fitting into an applicator, and the third body segment 35 which is the plastic needle over-moulded by the first body segment 20 and the second body segment 30. The device 10 is preferably made in one process by twin-shot injection moulding wherein the plastic needle 35 is first moulded with a first material and subsequently the first body segment 20 and the second body segment 30 are over-moulded on the plastic needle 35. The exposure of plastic needle 35 is achieved by pulling off the first body segment 20 linearly away from the second body segment 30 using a thumb and an index finger. FIGS. 2 and 3 respectively show the plan view and the side view of the plastic blood lancet 10 with and without the first body segment 20 on the plastic needle 35.

Figure 4:
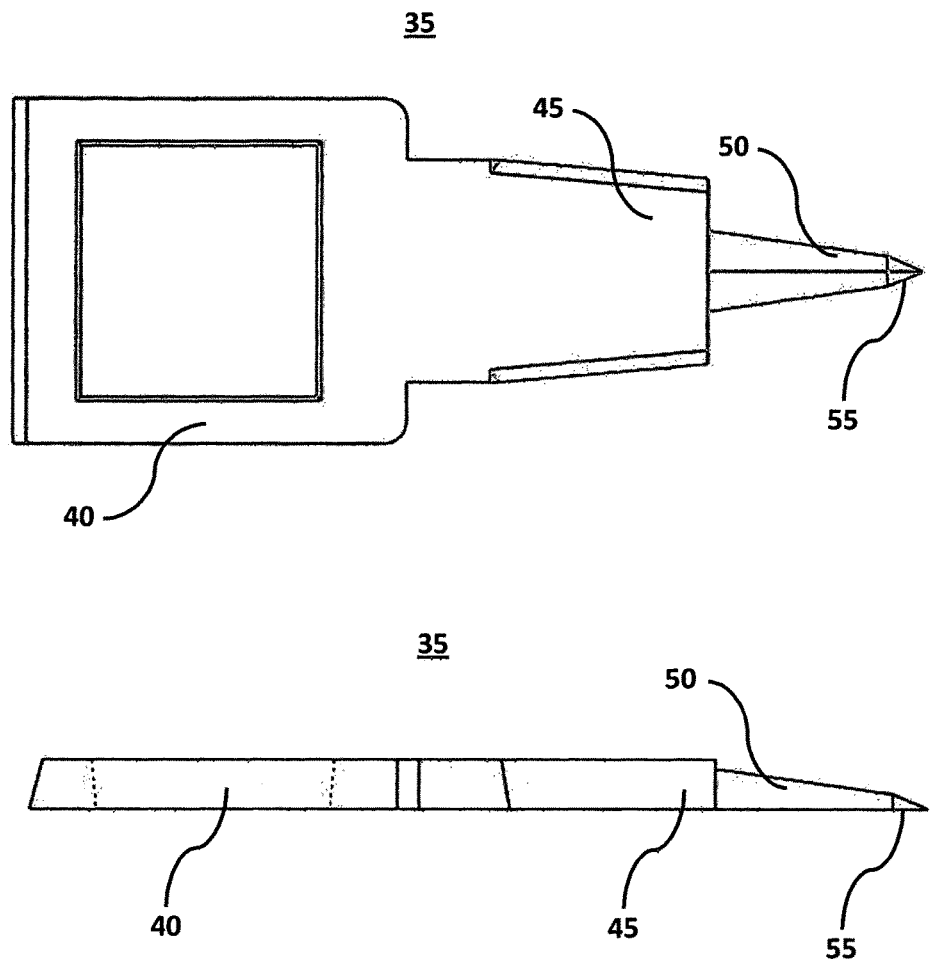
FIG. 4 illustrates a plan view and a side view of an alternate embodiment of a plastic needle

FIG. 4 shows the plastic needle 35 with square hole to act as an anchor 40 such that the plastic needle can be fixed or fastened or anchored onto the second body segment 30, a rectangular segment 45 to act as a slider for the first body segment 20 and to prevent any twisting movement between the plastic needle 35 and the first body segment 20, and the plastic needle tip 50. It is worth mentioning that the anchor 40 can have any form in addition to a square hole so long as the anchoring function can be achieved. It is also worth mentioning that the rectangular segment 45 can take any form so long that it is substantially flat in geometry so that the flat structure will prevent any twisting and will provide a linear pathway for the pulling of the first segment body 20 away from the second body segment 30. There is an apex 55 at the distal end of the plastic needle tip 50, which is bevelled to provide sharpness for penetrating the skin. The apex 55 has a much larger taper angle than that of the needle tip 50. From the plan view, the plastic needle tip 50 and the apex 55 are triangular, this shape will form a wider opening compared to a conical shape for the same depth. The total height of the plastic needle tip 50 plus the apex 55 is conventionally 3 mm, but the present invention is not limited to only this height. In one embodiment, the height of the plastic tip 50 is 2.5 mm and the height of the apex 55 is 0.5 mm. The biggest dimension of the needle tip 50 is at its base, which normally has a range from 0.7 mm to 1 mm. This dimension cannot be smaller than 0.4 mm; otherwise the needle may not have enough strength for skin penetration.

A preferred method for manufacturing the device 10 is by twin-shot injection moulding. Materials used for injection moulding the device 10 should be bio-compatible and gamma-irradiation stable. In addition, the polymer for moulding the plastic needle 35 should have sufficient impact and flexural strength. Particularly important is that the glass transition temperature (the temperature that a polymer starts to soften) should be higher than the melting temperature to prevent distortion or deformation of the plastic tip. One identified material that has all the characteristics is polyether-imide (PEI), which has a glass transition temperature of 220° C.

On the other hand, the polymer for moulding the first body segment 20 and the second body segment 30 does not require high impact and flexural strength but has to have a low melting temperature so that the heat will not affect the shape of the plastic needle 35 during the second moulding process. Another important condition is that there should be no chemical bonding present between the first material PEI and the second material, otherwise the first body segment 20 cannot be removed to expose the plastic needle 35. One identified polymer is high density polyethylene (HDPE), which has a melting temperature of 130° C. and does not have covalent bonding after the over-moulding process. The low melting temperature is good for a stable moulding process because under normal circumstance the polymer melt is normally raised to higher temperature to enhance flowability of the polymer melt. The wide gap between the melt temperature of HDPE and the glass transition temperature of PEI provides a good range of process window under which the over-moulding can be operated.

Advantages of the Present Invention

The first advantage of the present invention is that there is a square hole to act as an anchor 40 for the plastic needle 35 to be fixed on the second body segment 30 to eliminate the possibility of the needle slipping out of the second body segment 30 due to vibration or raised temperature during transportation or storage.

Another advantage of the present invention is the plastic tip 50 can be disabled by pressing it to a hard surface. The plastic needle 50 and the apex 55 will be bent and distorted posing no harm to the users. After the disablement act, the device can no longer be used for puncturing the skin, thereby eliminating the risk of re-use.

The third advantage of the present invention is the production efficiency. There is only one process involved in making the present invention, i.e. injection moulding. The plastic needle 50 and the first 20 and second 30 body segments can be injection moulded out using one twin-shot injection moulding machine. Since the two moulding processes are carried out at the same time and not in series, i.e. the first moulding of the plastic needle 50 and the second over-moulding of the first and second body segments 20 and 30 are carried out concurrently, the cycle time is greatly reduced thereby saving a lot of time and labour for handling and processing.

The fourth advantage of the present invention is that the present invention provides a strong plastic needle 50 with PEI, which will not deform or form covalent bonding (chemical bonding) with the second material HDPE under high moulding temperature and injection pressure. The wide gap between the PEI's glass transition temperature and the HDPE's melting temperature provides a good process window under which the over-moulding can take place, thereby giving a very stable and effective process.

The fifth advantage of the present invention is that the cap (or the first body segment) 20 is pulled off straight to expose the plastic needle tip 50 and apex 55, this is ensured by the rectangular body 45 guiding the linear movement. There is no twisting movement because the rectangular body 45 does not allow any twisting of the cap 30 given its flat structure. The plastic needle tip 50 and apex 55 will not be subjected to twisting or lateral movement which may lead to deformation or damage of the needle.

Bench Testing: 0.4 mm Polyurethane Foil Penetration Test 10 samples of the present invention were loaded in a normal applicator to penetrate polyurethane foils (hardness of Shore A82) of thicknesses 0.40 mm, which had 10 mm diameter of area of free tension. The penetration speed was estimated to be 60,000 mm/min. The penetration of foil was checked to confirm penetration by the plastic needle 35, and the apex 55 condition of was observed. For those samples that penetrated the PU foil without tip damage, they were used to repeatedly penetrate the foil for 3 more times. The results are summarized in Table 1 below:

TABLE 1

Matrix of Penetration Test

| | $1^{st}$ Penetration | $2^{nd}$ Penetration | $3^{rd}$ Penetration | $4^{th}$ Penetration |
|---|---|---|---|---|
| Sample 1 | Pass | Pass | Pass | Pass |
| Sample 2 | Pass | Pass | Pass | Pass |
| Sample 3 | Pass | Pass | Pass | Pass |
| Sample 4 | Pass | Pass | Pass | Pass |
| Sample 5 | Pass | Pass | Pass | Pass |
| Sample 6 | Pass | Pass | Pass | Pass |
| Sample 7 | Pass | Pass | Pass | Pass |
| Sample 8 | Pass | Pass | Pass | Pass |
| Sample 9 | Pass | Pass | Pass | Pass |
| Sample 10 | Pass | Pass | Pass | Pass |

It can be clearly shown that the present invention with the choice of materials is effective.

What is claimed is:

1. A plastic blood lancet comprising:

a) a first body segment, and b) a second body segment, both the first and second body segments being made from a second material at the same time, and which has a melting temperature that is lower than the glass transition temperature of a first material, and which does not form covalent bonding or have a chemical reaction with the first material, c) a plastic needle covered by the first body segment and made from the first material that has a glass transition temperature, the-plastic needle further comprising i) a hole portion disposed proximate to a first end of the plastic needle for anchoring the plastic needle onto the second body segment, ii) a rectangular section disposed between the hole portion and a needle tip for providing a sliding means for the first body segment to be pulled, and for preventing the first body segment to be twisted, iii) a needle tip having an apex at a distal end, the apex having a taper angle that is much larger than a taper angle of the needle tip, the apex being disposed proximate a second end of the plastic needle, the second body portion being overmoulded on the plastic needle.

2. A plastic blood lancet as in claim 1, wherein the first material comprises poly-ether-imide (PEI).

3. A plastic blood lancet as in claim 1, wherein the second material comprises poly-ethelene (HDPE).

4. A plastic blood lancet as in claim 1, wherein the first body segment can be removed to expose the plastic needle by pulling linearly away from the second body segment.

* * * * *